United States Patent [19]
Yang et al.

[11] Patent Number: 6,123,870
[45] Date of Patent: *Sep. 26, 2000

[54] STABLE OXIDIZING BROMINE FORMULATIONS, METHOD OF MANUFACTURE AND USES THEREOF FOR BIOFOULING CONTROL

[75] Inventors: Shunong Yang; William F. McCoy, both of Naperville; Anthony W. Dallmier, Aurora, all of Ill.

[73] Assignee: Nalco Chemical Company, Naperville, Ill.

[ * ] Notice: This patent is subject to a terminal disclaimer.

[21] Appl. No.: 09/296,212

[22] Filed: Apr. 21, 1999

Related U.S. Application Data

[63] Continuation-in-part of application No. 09/106,602, Jun. 29, 1998.

[51] Int. Cl.[7] .................................................. C01B 7/09
[52] U.S. Cl. .................... 252/186.1; 252/186.44
[58] Field of Search ................... 210/754, 758; 252/186.1, 186.44, 187.1, 187.2; 423/462, 466, 467

[56] References Cited

U.S. PATENT DOCUMENTS

| | | |
|---|---|---|
| 3,222,276 | 12/1965 | Belohlav et al. . |
| 3,493,654 | 2/1970 | Goodenough et al. . |
| 3,558,503 | 1/1971 | Goodenough et al. . |
| 4,131,556 | 12/1978 | Klopotek et al. ............... 252/106 |
| 4,759,852 | 7/1988 | Trulear . |
| 4,992,209 | 2/1991 | Smyk et al. . |
| 5,264,136 | 11/1993 | Howarth et al. . |
| 5,415,803 | 5/1995 | Shorr .......................... 252/186.44 |
| 5,589,106 | 12/1996 | Shim et al. . |
| 5,603,840 | 2/1997 | Strittmatter et al. . |
| 5,683,654 | 11/1997 | Dallmier et al. . |
| 6,007,726 | 12/1999 | Yang et al. ....................... 210/752 |

FOREIGN PATENT DOCUMENTS

| | | |
|---|---|---|
| 0 168 253 A2 | 1/1986 | European Pat. Off. . |
| WO96/30562 | 10/1996 | WIPO . |
| WO97/20909 | 6/1997 | WIPO . |
| WO97/43392 | 11/1997 | WIPO . |
| WO 99/62339 | 12/1999 | WIPO . |

*Primary Examiner*—David A. Simmons
*Assistant Examiner*—Betsey J. Morrison
*Attorney, Agent, or Firm*—Kelly L. Cummings; Thomas M. Breininger

[57] ABSTRACT

Stable oxidizing bromine compounds are prepared by preparing a caustic solution comprising a halogen stabilizer, water and an alkali or alkaline earth metal hydroxide, the halogen stabilizer being selected from the group consisting of $R-NH_2$, $R-NH-R^1$, $R-SO_2-NH_2$, $R-SO_2-NHR^1$, $R-CO-NH_2$, $R-CO-NH-R^1$ and $R-CO-NH-CO-R^1$ wherein R is a hydroxy group, an alkyl group or an aromatic group and $R^1$ is an alkyl group or an aromatic group, adding bromine chloride to the solution while mixing the solution, and cooling the solution.

8 Claims, No Drawings

STABLE OXIDIZING BROMINE FORMULATIONS, METHOD OF MANUFACTURE AND USES THEREOF FOR BIOFOULING CONTROL

REFERENCE TO RELATED PATENT

This application is a continuation-in-part of co-pending U.S. Ser. No. 09/106,602, still pending filed on Jun. 29, 1998.

FIELD OF THE INVENTION

The present invention relates to formulations used in biofouling control in industrial water systems. More specifically, the present invention relates to methods of preparing stable oxidizing bromine formulations and their use in biofouling control in industrial water systems.

BACKGROUND OF THE INVENTION

While elemental liquid bromine is an effective biocide, its low solubility (<4 g/100 g water), low boiling point (54.3° C.), high vapor pressure (214 mm Hg at 25° C.) and extreme corrosivity limit its use as a biocide in industrial applications. Another oxidizing bromine compound, bromine chloride, has slightly higher water solubility but is more volatile than elemental bromine. One other oxidizing bromine compound, bromate, is very toxic to mammals and is a suspected carcinogen. Nonoxidizing inorganic bromine compounds, such as bromide, have little or no antimicrobial activity.

A mixture of an aqueous bromine solution and a bromine stabilizer has been used to generate stable oxidizing bromine compounds for use as a biocide. An unstabilized aqueous bromine solution is very acidic, unstable and emits very pungent bromine fumes. The concentration of stabilized hypobromite solution that can be made from liquid bromine, however, has been limited due to the low solubility of bromine in water.

It has also been suggested that, in addition to a bromine stabilizer, an oxidizer, such as hypochlorite, be added to activate the bromide to hypobromite. After the completion of the conversion of bromide to hypobromite, the hypobromite is stabilized by the addition of a halogen stabilizer, such as sulfamate. While this is an improved process with a higher level of oxidizing halogen content (around 14% as $Br_2$), this process still requires the separate step of synthesizing sodium hypobromite (NaOBr) as a bromine source. NaOBr is known to be very unstable and will rapidly disproportionate to bromide and bromate, both of which have little or no antimicrobial activity. In addition, because sodium hypochlorite (NaOCl) is used as an activation agent, the concentration of stabilized product is limited by the available concentration of NaOCl.

Also known are methods of generating bromine for on-site use. Such processes involve electrolytically converting bromate into active bromine compounds such as bromine, hypobromous acid, hypobromite ion and hydrogen tribromide under acidic conditions. However, because the above process generates bromine for on-site use, methods or measures for optimizing bromine stabilization are not addressed.

Therefore, methods of generating higher concentrations of stable oxidizing bromine formulations in a safer manner are needed.

SUMMARY OF THE INVENTION

The present invention satisfies the aforementioned needs by providing a method of generating a stable oxidizing bromine compound which includes the steps of preparing a caustic solution comprising a halogen stabilizer, water and an alkali or alkaline earth metal hydroxide, the halogen stabilizer being selected from the group consisting of R—$NH_2$, R—NH—$R^1$, R—$SO_2$—$NH_2$, R—$SO_2$—$NHR^1$, R—CO—$NH_2$, R—CO—NH—$R^1$ and R—CO—NH—CO—$R^1$ wherein R is a hydroxy group, an alkyl group or an aromatic group and $R^1$ is an alkyl group or an aromatic group, adding bromine chloride to the solution while mixing the solution, and cooling the solution.

DETAILED DESCRIPTION OF THE INVENTION

The method of the present invention calls for generating a stable oxidizing bromine compound which includes the steps of preparing a caustic solution comprising a halogen stabilizer, water and an alkali or alkaline earth metal hydroxide, adding bromine or bromine chloride to the solution while agitating the solution and cooling the solution.

In an embodiment, the halogen stabilizer is selected from the group consisting of R—$NH_2$, R—NH—$R^1$, R—$SO_2$—$NH_2$, R—$SO_2$—$NHR^1$, R—CO—$NH_2$, R—CO—NH—$R^1$ and R—CO—NH—CO—$R^1$ wherein R is a hydroxy group, an alkyl group or an aromatic group and $R^1$ is an alkyl group or an aromatic group. Preferred halogen stabilizers include saccharin, benzenesulfonamide, urea, thiourea, creatinine, cyanuric acids, alkyl hydantoins, mono or di ethanolamine, organic sulfonamides, biuret, sulfamic acid, organic sulfamates and melamine.

In an embodiment, the caustic solution has a pH greater than 13 after the addition of bromine or bromine chloride.

In an embodiment, the step of adding bromine or bromine chloride is further characterized as adding bromine or bromine chloride in a molar amount approximately equal to the molar amount of halogen stabilizer and approximately equal to one-half of the molar amount of alkali or alkaline earth metal hydroxide.

In an embodiment, the solution is cooled to a temperature of less than 25° C.

In an embodiment, the step of adding bromine or bromine chloride is performed without exposing the bromine or bromine chloride to air.

In an embodiment, an alkali or alkaline earth metal hydroxide is added to the solution after the addition of bromine or bromine chloride to increase the pH of the solution above 13.

In an embodiment, the present invention provides an aqueous biocide solution containing a stable oxidizing bromine formulation. The solution comprises at least one oxidizing bromine compound selected from the group consisting of $^-SO_3NHBr$ and $^-SO_3NBr_2$ when sulfamate is used as the bromine stabilizer and a base in an amount sufficient to raise the pH of the solution to a level greater than 13.

In an embodiment, the base in the solution is an alkali or alkaline earth metal hydroxide.

It is therefore an advantage of the present invention to generate a stable oxidizing bromine solution using liquid elemental bromine or bromine chloride in a safe and efficient manner whereby no bromine or bromine chloride fumes are generated.

It is another advantage of the present invention to generate a higher concentration of stabilized hypobromite without the need for a separate step for hypobromite generation.

Another advantage of the present invention is that it provides a method for generating water soluble solid stable oxidizing bromine compounds.

Still another advantage of the present invention is that it provides a method for generating stable oxidizing bromine compounds without unwanted by-products such as high levels of bromate.

Yet another advantage of the present invention is that it provides stable oxidizing bromine compounds that are safer to transport and that are non-acidic.

Yet another advantage of the present invention is that it generates stable oxidizing bromine compounds for biofouling control in industrial water systems that are more compatible with other water treatment chemicals than unstabilized oxidizing bromine compounds.

The industrial water systems include cooling water systems, cooling ponds, reservoirs, sweetwater applications, decorative fountains, pasteurizers, evaporative condensers, hydrostatic sterilizers and retorts, gas scrubber systems and air washer systems.

Another advantage of the present invention is that it provides an improved method of biofouling control in pulp and paper processing systems.

Another advantage of the present invention is that it provides an improved method of biofouling control occurring on the surfaces of equipment in contact with produced oil field waters.

Another advantage of the present invention is that it provides an improved method of biofouling control in a food processing system.

Yet another advantage of the present invention is that it provides improved biofouling control in a beverage processing system.

Still another advantage of the present invention is that it provides improved biofouling control in a recreational water system.

Another advantage of the present invention is that it provides an improved method of disinfecting a hard surface.

Another advantage of the present invention is that it provides an improved bleaching method for the laundering of soiled garments and for the manufacture of cellulosic materials.

And, another advantage of the present invention is that it provides an improved method of washing food items, such as fruit and other food items.

Other objects and advantages of the present invention will be apparent upon a review of the following detailed description and appended claims.

EXAMPLES

The following examples are intended to be illustrative of the present invention and to teach one of ordinary skill how to make and use the invention. These examples are not intended to limit the invention or its protection in any way.

Example 1

Liquid bromine or bromine chloride is used as both oxidizer and bromine source. Sulfamate or other nitrogen base compounds are used as stabilizers. In addition, an adequate amount of alkali or alkaline earth metal hydroxide is required to maintain product pH. Formulation temperature is also extremely critical in insuring the formation of stable oxidizing bromines. Without adequate pH and temperature control, the heat generated by the exothermic reaction will cause rapid decomposition of the oxidizing species.

The process of making high concentration stable oxidizing bromine formulations consists of two steps. In the first step, a caustic stabilizing solution is prepared by mixing sulfamic acid, water and alkali or alkaline metal hydroxides (preferably NaOH, $Mg(OH)_2$ or other hydroxides). The pH of the alkali or alkaline earth metal sulfamate solution is higher than 14. Excess hydroxides are purposely added to neutralize the acids generated by the subsequent bromination step and to maintain a high pH (preferably greater than 13) in the finished product. The preferred molar ratio of sulfamate to liquid bromine or bromine chloride is 1:1. The preferred molar ratio of hydroxide to liquid bromine or bromine chloride is 2.2:1. The stabilizer solution can also be obtained by dissolving alkali or alkaline metal sulfamate in water and adding an appropriate amount of hydroxide.

The process is normally carried out in a jacketed glass reactor equipped with a proper mixing device. A cooling system for the reactor should be set up so that the reactor temperature can be controlled at an optimal range. An excessively high reaction temperature during the bromination step will accelerate sulfamate hydrolysis and cause decomposition of the desired product.

The second step of the process is to slowly add liquid bromine or bromine chloride into the stabilizer solution under good agitation. Bromine or bromine chloride is preferably added directly into the stabilizer solution through a Teflon® tube to prevent the volatilization of elemental bromine or bromine chloride. The addition rate is controlled so that the reaction temperature is preferably below 25° C. The higher the reaction temperature, the lower the product yield. If the reaction temperature gets over 35° C., sulfamate will start hydrolyzing into sulfate and ammonium. The resulting ammonium will react with and consume hypobromite and produce nitrogen gas which can be observed as vigorous foaming. With proper addition rates of liquid bromine or bromine chloride, the liquid bromine or bromine chloride will react instantaneously and will be stabilized. The process does not produce detectable bromine or bromine chloride fumes.

The product made with the above-described process was found to include no detectable bromate (less than 50 ppm with ion chromatography analysis); no detectable product concentration change was observed during a 2 month storage period at room temperature. For a 16.2% (as $Br_2$) product, the product has a half life of 74.5 days at 57° C.

Example 2

By way of an example, synthesis of a stable oxidizing bromine product using the above-described method is achieved by mixing 52.16 grams of sulfamic acid, 42.0 grams of water and 128.0 grams of 50% aqueous NaOH in a 500 ml three-neck glass reactor. The mixture is cooled to a temperature of about 3° C. under constant agitation and refrigerated in a water bath. 82.5 grams of liquid bromine (99.8% $Br_2$) is slowly added to the solution and the reaction temperature is controlled and maintained below 10° C. The resulting solution has a pH of 12.5. The solution pH was increased to a level greater than 13 by adding 3.0 grams of 50% NaOH. The bromine content in the resulting solution was 26.2% as $Br_2$ while a theoretical content if 100% conversion is achieved is 27.0% as $Br_2$.

After overnight storage at room temperature (21° C.), the formation of large amounts of crystals was observed in the solution. Using a 0.45 µm filter to separate the crystal from the liquid, followed by dehydration of the crystals under vacuum overnight, 46.8% as $Br_2$ was detected in the solid product while 18.7% of bromine content as $Br_2$ remained in the liquid. The solid product was found to be extremely water soluble. Accordingly, the present invention provides a solid stable oxidizing bromine product which is water soluble.

The solid product obtained in the above example has a very high concentration of stable oxidizing bromine compounds. The remaining content is believed to be water, excess NaOH and NaBr.

In an embodiment, the stable oxidizing bromine compound of the present invention can be used to provide improved biofouling control in industrial water systems, pulp and paper processing systems, food and beverage processing systems and recreational water systems. The stable oxidizing bromine compound of the present invention can also be used as a bleaching agent and to disinfect a hard surface. By way of example only, the present invention may be added to an aqueous media used to transport food through various processing systems and also to disinfect process equipment and waste water streams.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method of generating a stable oxidizing bromine compound, the method comprising the following steps:
    preparing a caustic solution comprising a halogen stabilizer, water and an alkali or alkaline earth metal hydroxide, the halogen stabilizer being selected from the group consisting of $R-NH_2$, $R-NH-R^1$, $R-SO_2-NH_2$, $R-SO_2-NHR^1$, $R-CO-NH_2$, $R-CO-NH-R^1$ and $R-CO-NH-CO-R^1$ wherein R is a hydroxy group, an alkyl group or an aromatic group and $R^1$ is an alkyl group or an aromatic group,
    adding bromine chloride to the solution while mixing the solution, and
    cooling the solution.

2. The method of claim 1 wherein the halogen stabilizer is selected from the group consisting of saccharin, benzenesulfonamide, urea, thiourea, creatinine, cyanuric acids, alkyl hydantoins, monoethanolamine, diethanolamine, organic sulfonamides, biuret, sulfamic acid, organic sulfamates and melamine.

3. The method of claim 1 wherein the caustic solution has a pH after the addition of bromine chloride of greater than 13.

4. The method of claim 1 wherein the step of adding bromine chloride is further characterized as adding bromine chloride in a molar amount approximately equal to a molar amount of halogen stabilizer and approximately one-half of a molar amount of alkali or alkaline earth metal hydroxide.

5. The method of claim 1 wherein the cooling step is further characterized as cooling the solution to a temperature of less than 25° C.

6. The method of claim 1 wherein the step of adding bromine chloride is performed without exposing the bromine chloride to air.

7. The method of claim 1 further comprising the following step after the addition of the bromine chloride:
    adding an alkali or alkaline earth metal hydroxide to the solution to increase the pH of the solution above 13.

8. A method of generating a stable oxidizing bromine compound, the method comprising the following steps:
    preparing a caustic solution comprising a halogen stabilizer, water and an alkali or alkaline earth metal hydroxide, the halogen stabilizer being selected from the group consisting of saccharin, benzenesulfonamide, urea, thiourea, creatinine, cyanuric acids, alkyl hydantoins, monoethanolamine, diethanolamine, organic sulfonamides, biuret, sulfamic acid, organic sulfamates and melamine,
    adding bromine chloride to the solution in a molar amount approximately equal to a molar amount of halogen stabilizer and approximately one-half of a molar amount of alkali or alkaline earth metal hydroxide and without exposing the bromine chloride to air,
    mixing the solution,
    cooling the solution to a temperature of less than 25° C., and
    adding an alkali or alkaline earth metal hydroxide to the solution to increase the pH of the solution above 13.

* * * * *